United States Patent [19]

Kantor et al.

[11] Patent Number: 4,650,802

[45] Date of Patent: Mar. 17, 1987

[54] METHODS AND COMPOSITIONS FOR TREATING PROTOZOAL INFECTIONS WITH A NOVEL ANTIBIOTIC

[75] Inventors: Sidney Kantor, Cranbury; Robert L. Kennett, Jr., Lambertville, both of N.J.

[73] Assignee: American Cyanamid Company, Stamford, Conn.

[21] Appl. No.: 593,162

[22] Filed: Mar. 26, 1984

[51] Int. Cl.[4] .............................................. A61K 31/44
[52] U.S. Cl. .................................................... 514/279
[58] Field of Search ......................................... 514/279

[56] References Cited

U.S. PATENT DOCUMENTS 4,277,478 7/1981 Zahner et al. ...................... 424/258

Primary Examiner—Frederick E. Waddell
Attorney, Agent, or Firm—Alice C. Brennan

[57] ABSTRACT

The present invention relates to methods and compositions for the control of protozoal infections, especially coccidial ones, in warm-blooded animals, such as meat-producing animals, i.e., poultry, by administering to the animals a protozoacidally-effective amount of a new antibiotic designated LL-D42067α, NRRL 15734. This novel antibiotic is produced via a controlled conditioned microbiological fermentation using a new strain of *Actinomadura madurae* subspecies *simaoensis* or mutants thereof.

8 Claims, 5 Drawing Figures

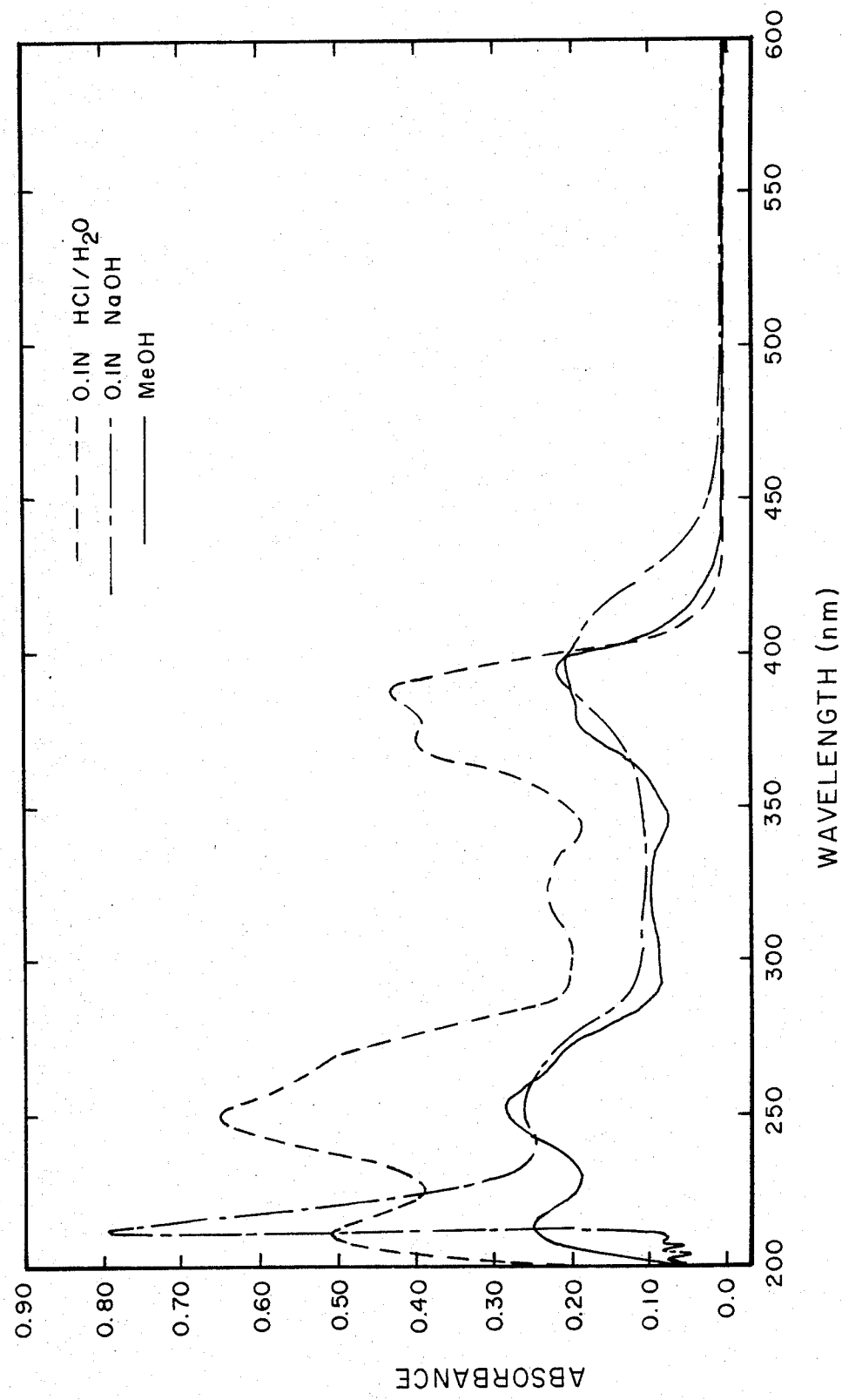
FIGURE I

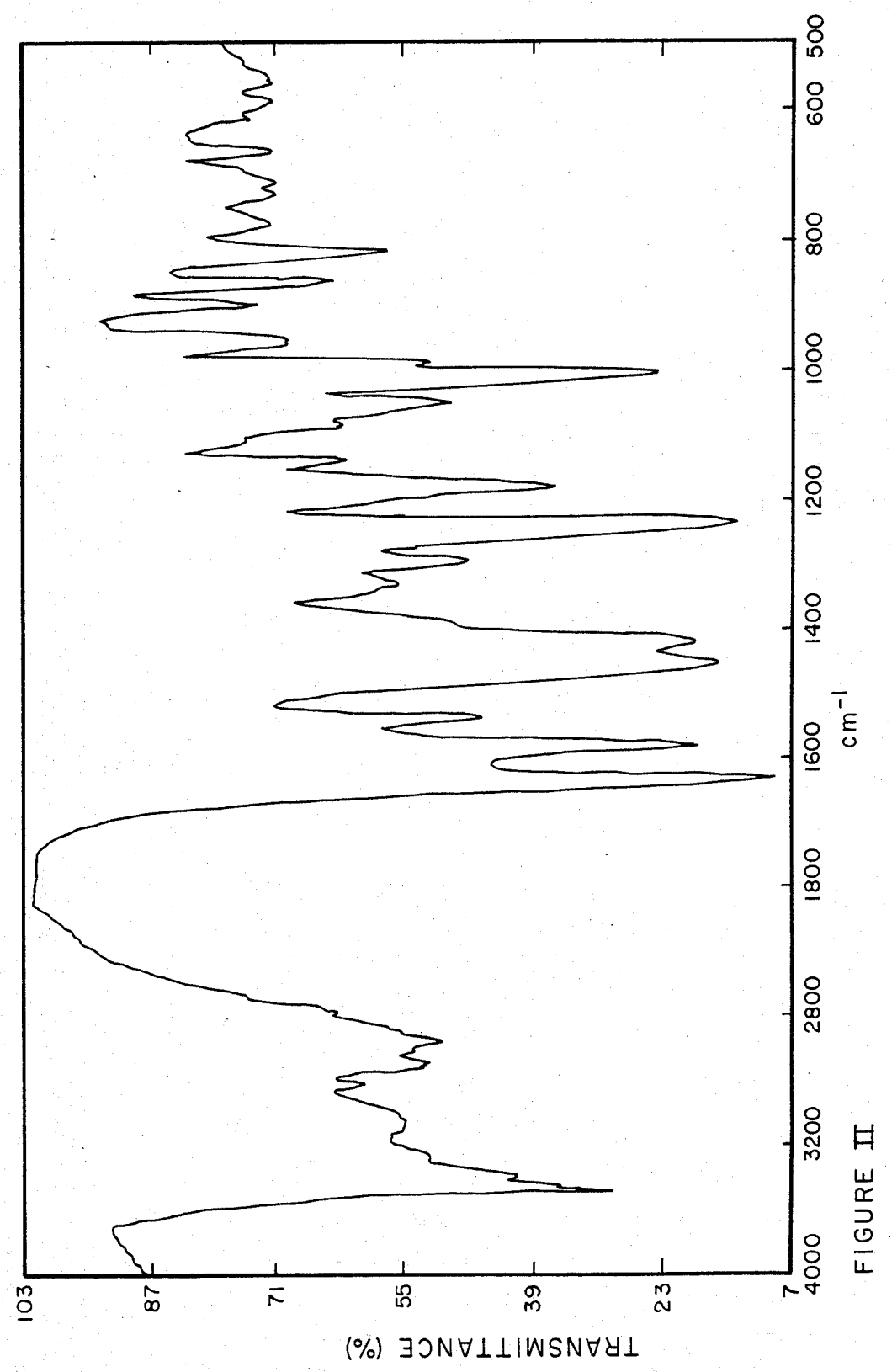

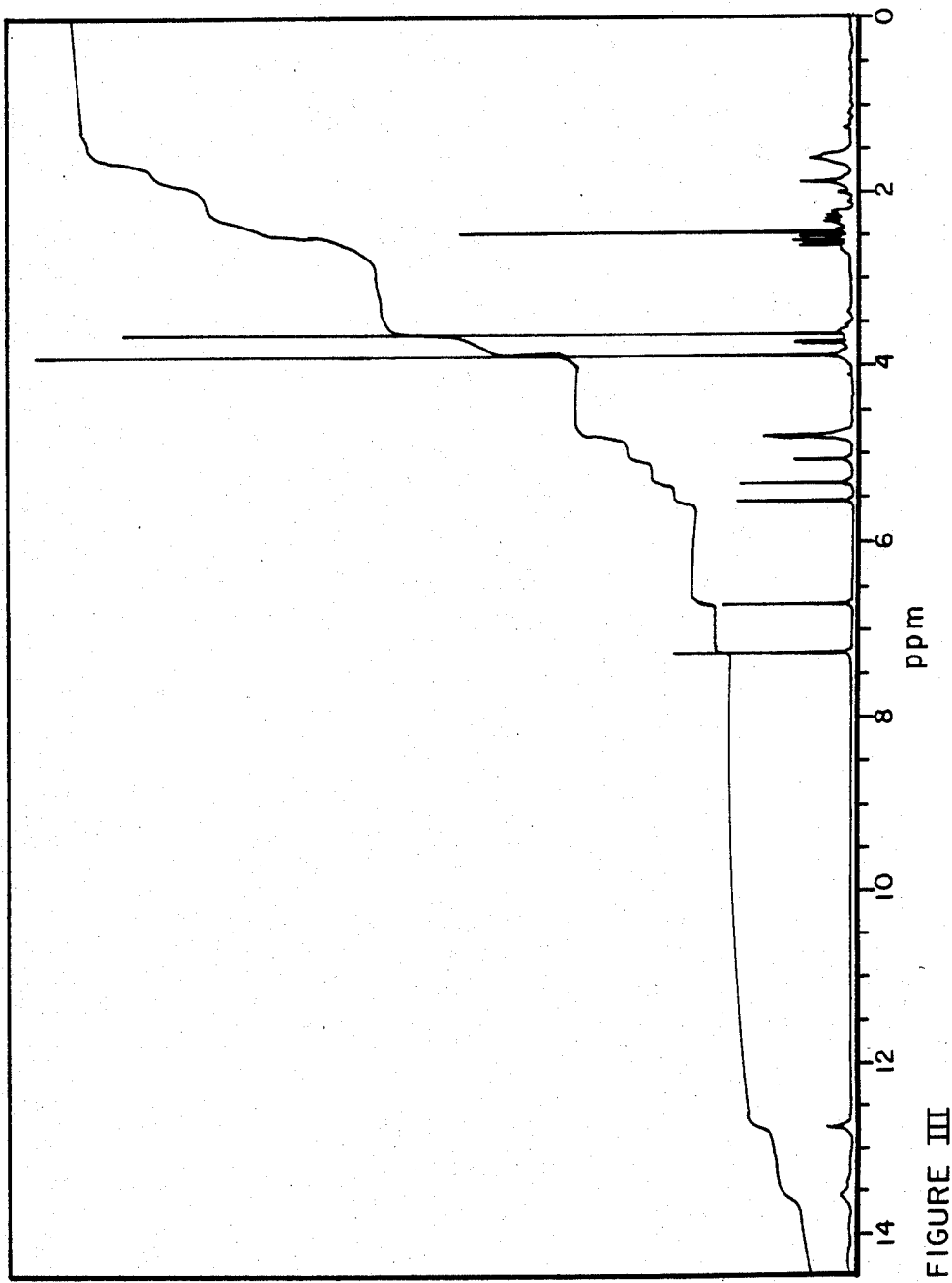
FIGURE III

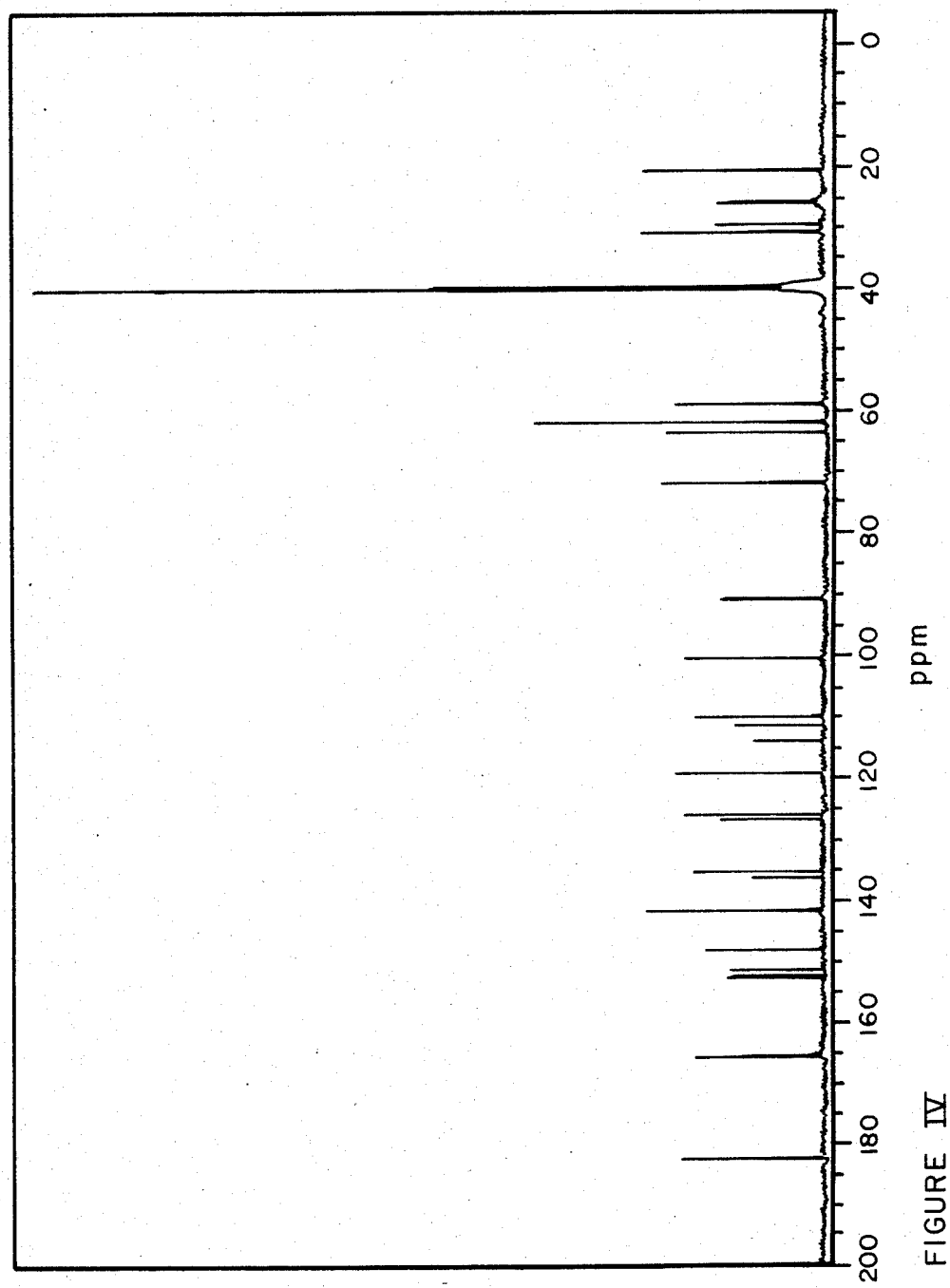
FIGURE IV

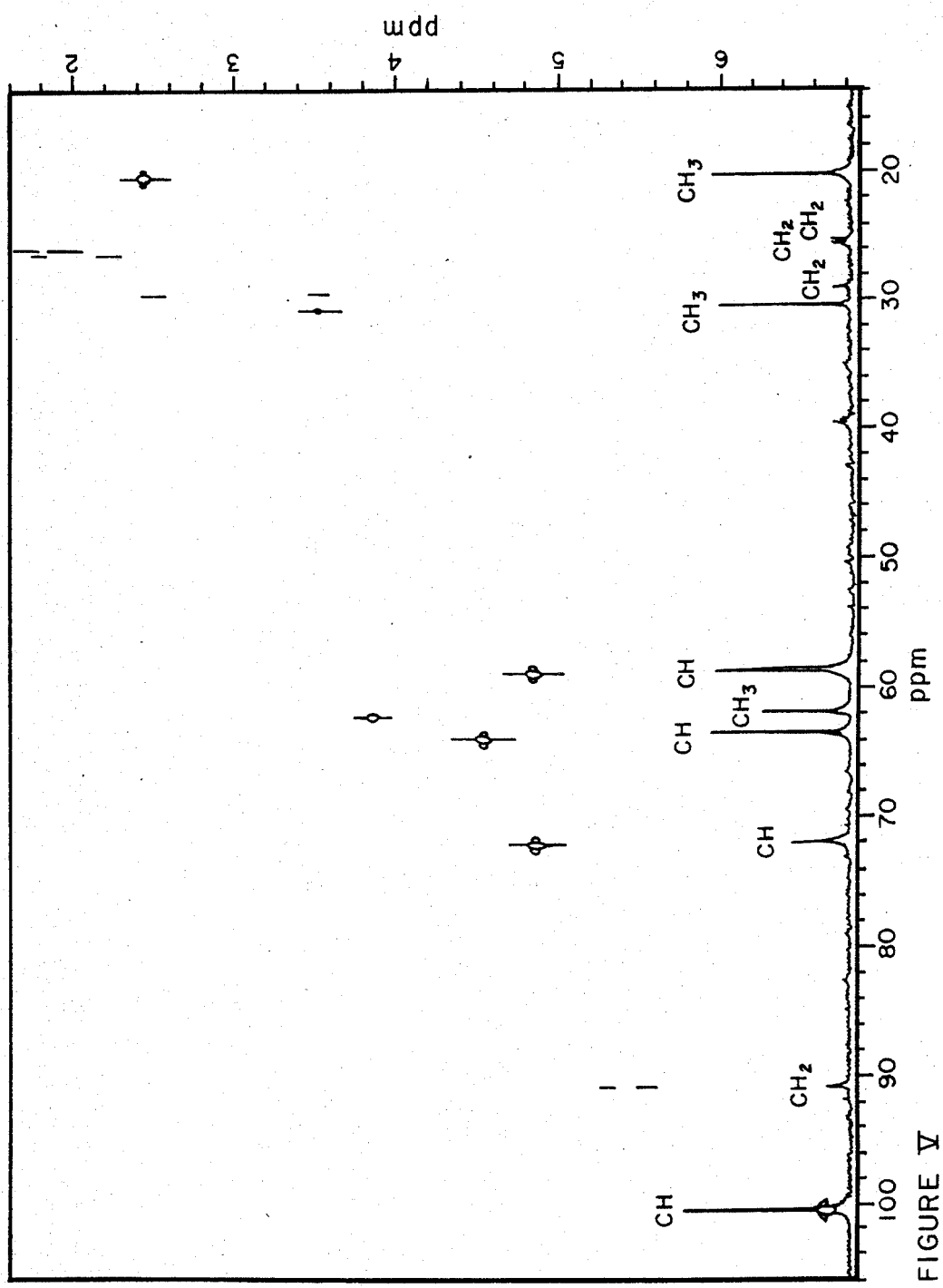
FIGURE V

METHODS AND COMPOSITIONS FOR TREATING PROTOZOAL INFECTIONS WITH A NOVEL ANTIBIOTIC

BACKGROUND OF THE INVENTION

The present invention relates to methods and compositions for preventing, treating, or controlling protozoal infections in warm-blooded animals by administering thereto an effective amount of the antibiotic LL-D42067α.

Coccidiosis is one of the most important of the protozoan parasitic diseases which plague the meat-producing industry. It is responsible for significantly greater losses to the poultry industry than from any other protozoan disease and is likewise responsible for substantial economic loss among a wide variety of farm, companion, and game animals.

This disease is caused by protozoan parasites which infect the host animals causing them to lose weight, reduce their feed efficiency; and, in many instances, die. In poultry, these protozoan parasites are generally of the genus Eimeria; six species of which have been shown to be primary causative agents for the disease in poultry. These six species are: *Eimeria tenella, Eimeria necatrix, Eimeria mivati, Eimeria maxima, Eimeria brunetti*, and *Eimeria acervulina*.

Although coccidiosis has been recognized, for many years, as one of the most important diseases confronting the meat-producing industry, nevertheless, heretofore no entirely satisfactory method of control of the disease has been provided.

Anticoccidial treatments which have met with some acceptance by the poultry industry are the compounds described in the E. Waletzky et al., U.S. Pat. No. Re. 26,833, reissued Mar. 24, 1970; and A. S. Tomcufcik, U.S. Pat. No. 3,769,432, issued Oct. 30, 1973, and the W. D. Celmer et al., U.S. Pat. No. 4,148,882, issued Apr. 10, 1979. The drugs described in the patents are useful for the treatment of coccidial infections in poultry; however, new, more effective treatments are still required if the industry is to successfully control the disease that challenges meat production throughout the world.

SUMMARY OF THE INVENTION

It is, therefore, an object of this invention to provide a novel method for the control of protozoan infections in warm-blooded animals, particularly meat-producing animals such as poultry, swine, cattle, rabbits, and sheep.

It is also an object of this invention to provide novel compositions effective for the control of protozoan infections in meat-producing animals.

The present invention relates to novel methods and antibiotic compositions effective for controlling, treating, minimizing, preventing, ameliorating, or curing protozoal infections in farm, companion, and game animals, particularly in meat-producing animals such as poultry, cattle, sheep, swine, and rabbits, and companion animals such as rabbits, dogs, and cats.

The antibiotic which is useful in the methods and compositions of this invention is LL-D42067α, NRRL 15734. This antibiotic and method for the preparation thereof are described in the United States Patent Application of Taikwang Michael Lee, Donald Bruce Borders, Joseph Jacob Goodman, Raymond Thomas Testa, and William Michael Maiese, Ser. No. 593,160, filed concurrently herewith and incorporated herein by reference thereto now U.S. Pat. No. 4,551,533. This antibiotic, designated LL-D42067α, NRRL 15734, has the following structural formula:

[Structural formula of LL-D42067a]

DESCRIPTION OF DRAWINGS

FIG. I: Characteristic ultraviolet absorption spectra of compound designated LL-D42067α, NRRL 5734.

FIG. II: Characteristic infrared absorption spectrum of compound designated LL-D42067α, NRRL 15734.

FIG. III: Characteristic proton nuclear magnetic resonance spectrum of the compound designated LL-D42067α, NRRL 15734, in CDCl$_3$ solution.

FIG. IV: Characteristic carbon-13 nuclear magnetic resonance spectrum of compound designated LL-D42067α, NRRL 15734, in DMSO solution.

FIG. V: Characteristic proton to carbon-13 chemical shift correlation of compound designated LL-D42067α, NRRL 15734, DMSO solution.

DETAILED DESCRIPTION OF THE INVENTION

It has been discovered that the above-mentioned antibiotic is especially effective for controlling coccidiosis caused by Eimeria species in meat-producing animals, particularly in poultry such as chickens, turkeys, ducks, geese, quail, and pheasants, and in cattle, sheep, swine, and rabbits.

It is also anticipated that the antibiotic compositions of this invention will prove to be effective for controlling malaria, toxoplasmosis, and sarcosporidiosis in warm-blooded animals since the causative agents for such diseases are protozoan infections and are biologically related to Eimeria.

In practice, the present invention involves the method of preventing, controlling, or treating protozoal infections, such as coccidiosis, in warm-blooded animals by administering thereto, a prophylactically, pharmaceutically, or therapeutically effective amount of the antibiotic compound designated LL-D42067α, NRRL 15734, or a pharmaceutically and pharmacologically acceptable salt thereof.

Although administration of the compound for coccidiosis will generally be most practical in or with the feed or in the drinking water, the above-said compound, or a pharmaceutically and pharmacologically acceptable salt thereof, may also be administered to individual hosts in the form of tablets, drenches, gels, capsules, or the like, or by injection in the form of a paste, gel, pellet, or solution. These latter methods of administration are, of course, less practical for the treatment of large groups of animals, but they are quite practical for use on a small scale or on an individual basis.

When the antibiotic LL-D42067α is used as a prophylactic or therapeutic treatment for coccidiosis in poultry, generally about 0.1 ppm to 5.0 ppm, and preferably, 0.5 ppm to 1.5 ppm of the antibiotic LL-D42067α, administered in the diet or drinking water of the poultry, is effective for preventing, controlling, or inhibiting coccidiosis in said animals.

As previously indicated, the antibiotic LL-D42067α, or a pharmaceutically and pharmacologically acceptable salt thereof, may also be employed as a prophylactic, pharmaceutical, or therapeutic treatment for the control, prevention, or inhibition of protozoal infections in other warm-blooded animals such as cattle, sheep, and swine. Generally, about 1.0 ppm to 100 ppm, and preferably 5 ppm to 50 ppm, of the antibiotic is effective for controlling protozoal infections, such as coccidiosis, in these larger animals.

Medicated poultry feeds useful in the method of the present invention are usually prepared by thoroughly admixing about 0.00001% by weight to about 0.0005% by weight of the antibiotic LL-D42067α with a nutritionally balanced poultry feed, as for example, the chick feed described in the examples hereinafter.

Medicated cattle, sheep, or swine feed can be prepared in the same manner as described above for the poultry feed excepting that 0.0001% by weight to 0.01% by weight of the antibiotic is admixed with the cattle, sheep, or swine feed.

When using the compound of the invention for the prevention or control of coccidiosis, the active anticoccidial agent is generally first prepared as an animal feed premix. The premix usually contains a relatively high percentage of the anticoccidial agent and is generally blended with the animal's feed just prior to administration. If desired, the feed premix may also be applied as a top dressing for the animal's daily ration.

Feed premixes or concentrates, useful in the practice of the present invention, may be prepared by admixing about 0.1% to 5.0% by weight of the above-identified antibiotic, or a pharmaceutically and pharmacologically acceptable salt thereof, with about 99.9% to 95% by weight of a suitable carrier or diluent. Carriers suitable for use to make up the feed supplement compositions include the following: alfalfa meal, soybean meal, cottonseed oil meal, linseed oil meal, sodium chloride, calcium carbonate, calcium sulfate, cornmeal, cane molasses, urea, bone meal, corncob meal, rice hull meal, and the like. The carrier promotes an essentially uniform distribution of the active ingredient in the finished feed into which the supplement is blended. It thus performs an important function by ensuring proper distribution of the active ingredient, i.e., about 0.1 ppm to 100 ppm thereof, throughout the feed. This is equivalent to 0.00001% to 0.01% by weight of the active ingredient in the finished feed. In practice, usually one or more pounds of premix is added per ton of feed to obtain the desired level of antibiotic in the finished feed.

If the supplement or premix is used as a top dressing for feed, it likewise helps to ensure uniformity of distribution of the active material across the top of the dressed feed.

Since the compound of this invention and its pharmaceutically and pharmacologically acceptable salts are relatively insoluble in water, it is generally desirable, when administering the compound in the animal's drinking water, to dissolve the active compound in an organic solvent such as methanol, ethanol, acetone, DMSO, oleic acid, linoleic acid, propylene glycol, or the like, and admix with the solution a small amount of surfactant and/or dispersing agent to assure solution and/or dispersion of the active ingredient in the animal's drinking water.

Advantageously, where the treatment of a small number of the larger meat-producing animals is required to control a protozoan infection therein, the antibiotic LL-D42067α or a pharmaceutically or pharmacologically acceptable salt thereof may be orally administered, on a daily basis, to the host animal in the form of a medicated gel.

The medicated gel may be prepared by admixing a medicated gellant phase with an aqueous buffer phase under reduced pressure 25–50 mm Hg at ambient temperature 20° C.–60° C. The gellant is prepared by dissolving or dispersing about 0.004% to about 4.5% by weight based on the final formulation of the antibiotic LL-D42067α or a pharmaceutically or pharmacologically acceptable salt thereof, in 14% to 31% by weight of propylene glycol based on the final formulation and about 15% to 50% by weight of the gellant at 60° C. to 80° C. Alternatively, the gellant phase may be prepared completely at ambient temperature as hereinafter described.

The gellant phase may be prepared by slurrying 0.004% by weight to about 4.5% by weight of the antibiotic LL-D42067α or a pharmaceutically or pharmacologically acceptable salt thereof, with the gellant 15% to 50%, and preferably 15% to 35% by weight of formulation in propylene glycol 14% to 30% by weight for 15 minutes to one hour under reduced pressure 25–50 mm Hg at room temperature. The gellant selected is a nonionic surfactant of structure α-hydro-Ω-hydroxy-poly(oxyethylene)poly(oxypropylene)-poly(oxyethylene) block copolymer, average molecular weight 12,500; mp 56° C.; Brookfield viscosity of 3,100 at 77° C.; surface tension of a 0.1% aqueous solution: 40.6 dynes/cm (measured with a du Nouy tensiometer).

An aqueous buffer solution may then be prepared by dissolving 1.5% by weight of citric acid and 1.0% by weight of trisodium citrate in about 3% by weight to about 25% by weight and preferably 6% to 12% by weight of final formulation in deionized or distilled water used in amounts of from about 15% by weight to about 50% by weight and preferably 35% to 45% by weight of formulation. This buffered solution provides a pH range at which long term chemical stability of the components of the gel formulation is achieved, i.e., pH 3–3.5.

Optional components which may be incorporated into the above solution at this stage are:

a. Benzyl alcohol added in amounts of from about 0.5% by weight to about 1.5% by weight and preferably 1.5% by weight of formulation as an antimicrobial preservative;

b. the yellow dye C.I. Acid yellow No. 23; ("tartrazine;" F. D. and C yellow No. 5; 4,5-dihydro-5-oxo-1-(4-sulfophenyl)-4-[(sulfophenyl)azo]-1H-pyrazole-3-carboxylic acid trisodium salt) used as coloring agent in amounts of from about 0.01% by weight to about 0.03% by weight and preferably 0.01% by weight of formulation;

c. an antifoaming agent comprising a mixture of dimethylpolysiloxanes of structure:

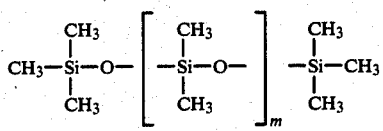

and silica gel, wherein the calculated average value of m is 200–350, the mixture is a water-white viscous oil-like liquid; d=0.965–0.970; $n_D^{25}$ about 1.404; viscosity about 60,000 centistrokes (and said antifoaming agent is described in U.S. Pat. No. 2,441,098) used in amounts of from 0.001–0.02% by weight and preferably 0.02% by weight of formulation.

The medicated gel is prepared by simply mixing either of the above-gellant phases and the aqueous solution from one-half to two hours under reduced pressure of from 10–100 mm Hg, and preferably 25–50 mm Hg, at ambient temperatures of from 20° C. to 60° C. without the requirements of either additional heating or cooling. This procedure gives an air-free gel which is suitable for administering exact dosages of anticoccidial by volume. When careful control of dosage of active ingredients to be administered by volume is not necessary, and when the presence of air in the gel is acceptable in the final formulation, the preparation may be carried out at pressures up to and including atmospheric pressure.

By the above method, a typical gel of the invention may be prepared by dissolving 4.5 g of the antibiotic LL-D42067α, 1.5 g citric acid monohydrate, 1.0 g sodium citrate dihydrate, 1.5 g of benzyl alcohol, and 0.01 g of the yellow dye C.I. Acid yellow No. 23 in 42 g of water. Next, a solution of the above gellant 28 g in propylene glycol 21.99 g is prepared by mixing at 60° C. Then the solutions are mixed together under 25–50 mm Hg until a homogeneous mixture is obtained at 20° C. to 60° C. without additional heating or cooling. The gel formed has a gelation temperature range of from −15° C. to −18° C.; viscosity of the gel is $0.51\times10^{+6}$; and the water gellant ratio is 1.5/1.0.

When 6.3 grams of this medicated gel are orally administered to a 200 pound (90.8 kg) fattening steer on a daily basis, said steer receives approximately 3 mg/kg of body weight/day of the protozoacidially-effective antibiotic LL-D42067α.

In practice, generally about 0.03 mg/kg/day to about 3.0 mg/kg/day is effective for controlling protozoan infections in cattle, sheep, and swine. For smaller companion animals, rates as low as 0.003 mg/kg of body weight/day may be employed.

The structure of LL-D42067α, shown above, has been elucidated by x-ray crystallography, and the relative stereochemistry of this compound is shown below.

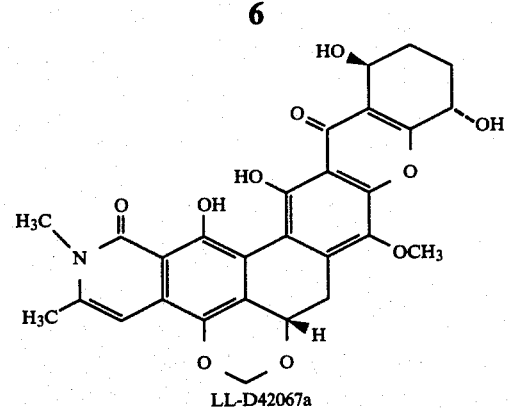

LL-D42067α

The physico-chemical characteristics of LL-D42067α are described below:
(1) Molecular weight: 535 (FAB-MS);
(2) Molecular formula: $C_{28}H_{25}NO_{10}$;
(3) Specific optical rotation: $[\alpha]_D^{26} = +836\pm40°$ (C 0.3, DMF);
(4) Ultraviolet absorption spectra: as shown in FIG. I
$UV_{MAX}^{CH3OH} =$
  215 nm (ε 13,200)
  254 nm (ε 15,000)
  320 nm (ε 5,100)
  395 nm (ε 11,400)
$UV_{MAX}^{0.1N\ HCl} =$
  213 nm (ε27,100)
  253 nm (ε 34,500)
  321 nm (ε 12,200)
  374 nm (ε 21,100)
  389 nm (ε 22,900)
$UV_{MAX}^{0.1N\ NaOH} =$
  217 nm (ε 42,100)
  253 nm (ε 13,900)
  312 nm (ε 5,700)
  395 nm (ε 10,700);
(5) Infrared absorption spectrum: as shown in FIG. II (KBr disc): 1650, 1598, 1543, 1470, 1440, 1260, 1195, 1020 cm$^{-1}$;
(6) Proton nuclear magnetic resonance spectrum (CDCl$_3$): as shown in FIG. III, and described in Table I;
(7) Carbon-13 nuclear magnetic resonance spectrum (DMSO): as shown in FIG. IV and described in Table II; and
(8) Proton to carbon-13 chemical shift correlation map (DMSO): as shown in FIG. V.

TABLE I

Proton NMR Data for LL-D42067α

| δ* | No. of Hydrogen** | Multiplicity*** | J (H) |
|---|---|---|---|
| 1.88 | 2 | m | |
| 2.34 | 2 | m | |
| 2.45 | 3 | s | |
| 2.58 | 1 | m | |
| 3.62 | 3 | s | |
| 3.72 | 1 | d,d | 4.64, 14.22 |
| 3.88 | 3 | s | |
| 4.80 | 2 | m | |
| 5.08 | 1 | m | |
| 5.32 | 1 | d | 5.81 |
| 5.55 | 1 | d | 5.81 |
| 6.70 | 1 | s | |
| 12.76 | 1 | s | |
| 13.58 | 1 | s | |

*CDCl$_3$, ppm downfield from TMS.
**Spectrum in DMSO-d$_6$, shows two additional absorptions at 4.55 (s) and 5.91 (d) ppm.
***s = singlet; d = doublet; t = triplet; m = multiplet.

TABLE II

Carbon-13 NMR Data for LL-D42067α

| Carbon | Chemical Shift (ppm)* | Carbon Type |
|---|---|---|
| 1 | 20.4 | $CH_3$ |
| 2 | 25.4 | $CH_2$ |
| 3 | 25.8 | $CH_2$ |
| 4 | 29.0 | $CH_2$ |
| 5 | 30.4 | $CH_3$ |
| 6 | 58.5 | CH |
| 7 | 61.6 | $CH_3$ |
| 8 | 63.3 | CH |
| 9 | 71.7 | CH |
| 10 | 90.4 | $CH_2$ |
| 11 | 100.0 | CH |
| 12 | 109.2 | q** |
| 13 | 109.7 | q |
| 14 | 111.0 | q |
| 15 | 113.7 | q |
| 16 | 119.0 | q |
| 17 | 125.8 | q |
| 18 | 126.6 | q |
| 19 | 134.9 | q |
| 20 | 135.3 | q |
| 21 | 136.1 | q |
| 22 | 141.3 | q |
| 23 | 147.9 | q |
| 24 | 151.1 | q |
| 25 | 152.5 | q |
| 26 | 165.4 | q |
| 27 | 165.6 | q |
| 28 | 182.3 | q |

*DMSO-$d_6$, ppm downfield from TMS.
**q = quarternary.

The protozoacidally-effective compound of this invention, designated LL-D42067α, is formed during the cultivation under controlled conditions of a new strain of a new subspecies of Actinomadura madurae. This new strain is maintained in the culture collection of the Medical Research Division, American Cyanamid Company, Pearl River, N.Y. as culture number LL-D42067α. A viable culture of this new microorganism has been deposited with the Patent Culture Collection Laboratory, Northern Regional Research Center, U.S. Department of Agriculture, Peoria, Ill. 61604, and has been added to its permanent collection. It is freely available to the public in this depository under its accession number NRRL 15734.

Culture LL-D42067α was isolated from a soil sample from San Simao, Brazil. The culture was taxonomically characterized and was identified as a new subspecies of Actinomadura madurae, designated Actinomadura madurae subspecies simaoensis.

Observations were made of the cultural, physiological and morphological features of the culture in accordance with the methods detailed by Shirling and Gottlieb [Intern. J. System. Bacteriol., 16:313–340 (1966)] and Gordon, et al. [Intern. J. System. Bacteriol., 24:54–63 (1974)]. The chemical composition of the cell walls of the culture was determined using the method of Lechevalier, et al. [Adv. Appl. Microbiol., 14:47–72 (1971)]. Details are recorded in Tables III–V, and a general description of the culture is given below. Underscored descriptive colors are taken from Kelly and Judd [Nat. Bur. Stand., Spec. Publ., 440 (1976)] and the accompanying Intersociety Color Council, National Bureau of Standards Centroid Color Charts.

GROWTH CHARACTERISTICS

Table III describes the cultural characteristics of culture LL-D42067α on various agar media which were selected from those recommended by the International Streptomyces Project Committee (hereinafter referred to as "ISP").

MICROMORPHOLOGY

Microscopic examination of the strain showed it to form short chains of conidia on aerial hyphae which were slightly hooked to short-spirals (up to three turns). The spore surfaces were smooth when observed by electron microscopy, distinguishing this isolate from A. verrucosopora.

CELL WALL COMPOSITION

Whole cell analyses showed the strain to contain meso diaminopimelic acid (DAP) and the sugar 3-O-methyl-D-galactose (madurose); thus it falls into whole cell pattern type B. The cell wall composition was of the type III (meso DAP, glutamic acid, alanine, muramic acid and glucosamine) and the phospholipid pattern of type PIV (phosphatidyl ethanolamine and/or methylethanolamine plus unknown glucosamine-containing phospholipids). These data support the assignment of the strain to the genus Actinomadura. The PIV phospholipid type is not typical for A. madurae, which is usually PI.

PHYSIOLOGICAL REACTIONS

The physiological reactions of strain LL-D42067α were examined using both the ISP system, Shirling and Gottlieb [Intern. J. Syst. Bacteriol., 16:313–340 (1966)] and the Gordon tests, Gordon, et al. [Intern. J. Syst. Bacteriol., 24:54–63 (1974)]. The utilization pattern of the strain on ISP carbohydrate media is given in Table IV, along with those of other members of the genus reacting similarly. Culture LL-D42067α resembles the Actinomadura madurae and Actinomadura verrucosopora groups. As indicated above, however, it differs from Actinomadura verrucosopora in having smooth spore walls. A comparison of reactions in the Gordon test series of Actinomadura madurae (Gordon's data; see reference above) and LL-D42067α, summarized in Table V, revealed differences only in amylase production and acid from glycerol and raffinose. Since amylase production and raffinose utilization have been found to be variable in Actinomadura madurae [Goodfellow, N., et al., J. Gen. Microbiol., 112:95–111 (1979)], the glycerol reaction remains the only physiological difference of LL-D42067α from this taxon.

Since strain LL-D42067α is the same as Actinomadura madurae in all properties evaluated except for its glycerol reaction and its PIV phospholipid pattern, it has been assigned to the taxon Actinomadura madurae as a subspecies designated Actinomadura madurae subspecies simaoensis.

TABLE III

Cultural Characteristics of LL-D42067α *Actinomadura madurae* subspecies *simaoensis* on ISP Morphological Media

| Agar Medium | Aerial Mycelium | Vegetative Mycelium | Soluble Pigment |
|---|---|---|---|
| Yeast extract, Malt extract (ISP 2) | White, sparse | Medium orange-brown-I53* | None |
| Inorganic Salts Starch (ISP 4) | Colorless | Colorless | None |
| Glucose Asparagine (ISP 5) | Colorless | Colorless | None |
| Oatmeal (ISP 3) | Sparse pinkish-white | Light orange-brown-I52* | None |

*I = ISCC Color charts

TABLE IV

Comparison of Carbohydrate Utilization Reactions of LL-D42067α With Related *Actinomadura spp.*

| Carbohydrate | LL-D42067α | A. madurae (a) | A. verrucosopora (a) (b) |
|---|---|---|---|
| L-arabinose | + | + | + |
| D-fructose | + | + | + |
| I-inositol | − | variable | variable |
| D-mannitol | + | + | + |
| raffinose | − | − | − |
| rhamnose | + | + | + |
| sucrose | + | + | + |
| D-xylose | + | + | + |

(a) Goodfellow, M., et al., J. Gen. Microbiol., 112:95–111 (1979).
(b) Nonomura, H. and O'Hara, Y., J. Ferm. Technol., 49:904–912 (1971).

TABLE V

Gordon Test Reactions of LL-D42067α

| | LL-D42067α | A. madurae (Gordon Data*) |
|---|---|---|
| Degradation/Transformation of | | |
| Casein | + | +(98) |
| Xanthine | − | − |
| Hypoxanthine | + | +(98) |
| Tyrosine | + | +(91) |
| Adenine | − | − |
| Production of | | |
| Amylase | − | + |
| Gelatinase | + | + |
| Phosphatase | − | ND |
| Nitrate Reductase | + | +(98) |
| Urease | − | − |
| Esculinase | + | +(98) |
| Growth on/in | | |
| 5% Sodium Chloride | − | ND |
| Salicylate | − | ND |
| Lysozyme Broth | − | −(91) |
| Utilization | | |
| Acetate | + | + |
| Benzoate | − | −(94) |
| Citrate | − | +(83) |
| Lactate | + | ND |
| Malate | + | +(84) |
| Mucate | − | − |
| Oxalate | − | ND |
| Propionate | − | ND |
| Pyruvate | + | ND |
| Succinate | + | +(83) |
| Tartrate | − | − |
| Growth at | | |
| 10° C. | − | − |
| 45° C. | + | −(66) |
| 53° C. | − | − |
| Acid from | | |
| Adonitol | + | +(91) |
| Arabinose | + | + |
| Cellobiose | + | + |
| Dextrin | + | ND |
| Dulcitol | − | − |
| Erythritol | − | − |
| Fructose | + | ND |
| Galactose | + | +(84) |
| Glucose | + | + |
| Glycerol | − | + |
| Inositol | − | +(60) |
| Lactose | − | +(55) |
| Maltose | − | +(53) |
| Mannitol | + | + |
| Mannose | + | +(94) |
| Melibiose | − | − |
| α-Methyl-D-glucoside | − | − |
| Raffinose | variable | − |
| Rhamnose | + | + |
| Salicin | + | ND |
| Sorbitol | − | − |
| Sucrose | + | ND |
| Trehalose | + | +(96) |
| Xylose | + | + |
| β-Methyl-D-xyloside | + | ND |

*Percentages of cultures showing reaction given in parentheses if not 100%.
ND = Not determined.

For the production of this new protozoacidally-effective agent, the present invention is not limited to this particular organism or to organisms fully answering the above growth and microscopic characteristics which are given for illustrative purposes only. In fact, it is desired and intended to include the use of naturally-occurring mutants of this organism as well as induced mutants produced from this organism by varius mutagenic means known to those skilled in the art such as exposure to nitrogen mustard, x-ray radiation, ultraviolet radiation, N'-methyl-N'-nitro-N-nitrosoguanidine, actinophages, and the like. It is also desired and intended to include inter- and intraspecific genetic recombinants produced by genetic techniques known to those skilled in the art such as, for example, conjugation, transduction, and genetic engineering techniques.

GENERAL FERMENTATION CONDITIONS

Cultivation of *Actinomadura madurae* subspecies *simaoensis* NRRL 15734 may be carried out in a wide variety of liquid culture media. Media which are useful for the production of this novel antibiotic LL-D42067α include an assimilable source of carbon, such as dextrin, sucrose, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone oil may be added as needed.

GENERAL PROCEDURE FOR THE ISOLATION OF LL-D42067α

The LL-D42067α antibiotic is recovered from the fermentation broth by filtration through diatomaceous earth, extracted into a solvent such as methylene chloride and purified by column chromatography on silica gel, using the system hexane:ethyl acetate (80:20) to remove unwanted fats and the methylene chloride:1% acetic acid in methanol (9:1) to give a crude product.

This crude LL-D42067α is then purified by high performance liquid chromatography on a reverse phase column using the system acetonitrile:water:acetic acid (600:400:0.28).

EXAMPLE 1

Inoculum Preparation

A typical medium used to grow the primary inoculum was prepared according to the following formula:

| | |
|---|---|
| Glucose | 1.0% |
| Dextrin | 2.0% |
| Yeast extract | 0.5% |
| N—Z Amine A ®[1] | 0.5% |
| Calcium carbonate | 0.1% |
| Water qs. | 100% |

[1] A pancreatic digest of casein, registered trademark of Sheffield Chemical, Norwich, New York]

This medium was adjusted to pH 7.2 and then sterilized. A 100 ml portion of this sterile medium, in a 500 ml flask, was inoculated with mycelial scrapings from an agar slant of *Actinomadura madurae* subspecies *simaoensis* NRRL 15734. The medium was then placed on a rotary shaker and agitated vigorously at 210 rpm for 48–72 hours at 28° C. This primary inoculum was then used to inoculate 12 liters of the same sterile medium which was then grown at 28° C. for 48 hours providing secondary inoculum.

EXAMPLE 2

Fermentation

A fermentation medium of the following formulation was prepared:

| | |
|---|---|
| Sucrose | 3.0% |
| Soy flour | 1.5% |
| Corn steep liquor | 0.5% |
| Calcium carbonate | 0.5% |
| Water qs. | 100% |

The medium was sterilized and inoculated at the rate of 12 liters of secondary inoculum from Example 1 per 300 liters of medium. The fermentation was conducted at 28° C. with a sterile air flow of 200 liters per liter of mash per minute, agitation by an impeller operated at 230 rpm for 135–159 hours at which time the mash was harvested and filtered through diatomaceous earth.

EXAMPLE 3

Isolation of LL-D42067α

The fermentation filtrate from three fermentations, conducted as described in Example 2, were combined, making a total of 1800 liters at pH 7.5, and extracted with 900 liters of methylene chloride. The organic phase was concentrated in vacuo to give 84.1 g of residue.

A 75.2 g portion of this residue was suspended in 300 ml of hexane:ethyl acetate (80:20) and allowed to seep into a glass column (2 inches×20 inches) dry packed with silica gel. The column was eluted with a total of 4 liters of the same solvent mixture in order to remove fats and silicone oil and was then eluted with 4 liters of methylene chloride:1% acetic acid in methanol (9:1) collecting 15 ml fractions. The fractions were analyzed by thin-layer chromatography. Antibiotic LL-D42067α appeared visually as a yellow spot (Rf=0.5) with the same solvent system. Fractions 31–60, which contained most of the antibiotic, were pooled and concentrated in vacuo, giving 11.1 g of a red residue.

A 5.5 g portion of the above residue was fractionated by high performance liquid chromatography [Prep LC System-500, Prep PAK-500/C18 cartridge, acetonitrile:water:acetic acid (600:400:0.28), 100 ml/minute, 5.5 g/30 ml/injection]. Thirty 200 ml fractions were collected. Analytical high performance liquid chromatographic analysis of the fractions showed the major portion of LL-D42067α was in fraction 5. Fraction 5 was allowed to stand overnight. The resulting yellow crystals were collected by decanting off the mother liquor (which was saved), washing the crystals with the mobile phase and air drying, giving 11 mg of LL-D42067α as yellow crystals.

The mother liquor was concentrated by slow evaporation. The resulting precipitate was collected by centrifugation giving 377 mg of LL-D42067α as a yellow amorphous solid.

The analytical HPLC conditions were:

Column: $\mu$ Bondapak C18, 3.9 mm×30 cm, Waters Associates
Mobile Phase: acetonitrile:water:acetic acid (400:600:0.28)
Detector: UV 254 nm and UV 365 nm, 0.2 AUFS
Flow Rate: 1.0 ml/minute
Retention Volume of LL-D42067α: 11.5 ml.

EXAMPLE 4

Evaluation of test compounds as anticoccidial agents

The usefulness of antibiotic LL-D42046α as an anticoccidial agent for chickens is demonstrated in the following tests.

The poultry diet employed in the test is as follows:
Vitamin-amino acid premix: 0.5%
Trace minerals: 0.1%
Sodium chloride: 0.3%
Dicalcium phosphate: 1.2%
Ground limestone: 0.5%
Stabilized fat: 4.0%
Dehydrated alfalfa, 17% protein: 2.0%
Corn gluten meal, 41% protein: 5.0%
Menhaden fish meal, 60% protein: 5.0%
Soybean oil meal, 44% protein: 30.0%
Ground yellow corn, fine to: 100.0%

The vitamin-amino acid premix in the above feed composition is prepared from the following formulation. The expressions of quantity relate to units per kilogram of the finished feed composition.
Butylated hydroxy toluene: 125.0 mg
dl-Methionine: 500.0 mg
Vitamin A: 3300.0 I.U.
Vitamin $D_3$: 1100.0 I.C.U.
Riboflavin: 4.4 mg
Vitamin E: 2.2 I.U.
Niacin: 27.5 mg
Panthothenic acid: 8.8 mg
Choline chloride: 500.0 mg
Folic acid: 1.43 mg
Menadione sodium bisulfate: 1.1 mg
Vitamin $B_{12}$: 11.0 mcg
Ground yellow corn, fine to: 5.0 gm A mixed inoculum of 5000 sporulated oocysts of *Eimeria acervulina* and a sufficient number of oocysts of *Eimeria tenella* to produce 60% to 75% mortality in untreated controls were given to one-day-old chicks, by direct inoculation into the crops of all chicks. The chicks were given free access to feed and water during the entire test period. Two days before inoculation, medicated feed with several levels of drug was presented to the various groups of chicks. Seven days after inoculation, the tests were terminated and the chicks were weighed, necropsied, and their intensinal tracts examined for lesions. The results appear in the Table below. These results show that improved survival of infected chicks is obtained when 0.2 ppm to 5.0 ppm of the antibiotic is administered to infected chicks in their diet. These levels also show a significant suppression of lesions due to E. tennela and E. acervulina.

group. The percent reduction of lesions was calculated as follows:

$$100 - \left( \frac{\text{treated score (pooled)}}{\text{control score (pooled)}} \times 100 \right)$$

The results appear in Table VII below. These results show that lesions from five species of Eimeria in chicks can be prevented or significantly reduced at concentrations of drug as low as 0.2 ppm in the diet.

TABLE VII
EVALUATION OF ANTIBIOTIC LL-D42067α FOR THE CONTROL OF COCCIDIOSIS IN CHICKS

| Compound | Concentration in Diet, ppm | No. Chicks Started | Percent Reduction of Lesions | | | | |
| --- | --- | --- | --- | --- | --- | --- | --- |
| | | | E. tenella | E. acervulia | E. brunetti | E. necatrix | E. maxima |
| LL-D42067α | 1.25 | 15 | 100 | 95 | 100 | 100 | 100 |
| LL-D42067α | 1.0 | 15 | 100 | 91 | 100 | 100 | 100 |
| LL-D42067α | 0.75 | 15 | 74 | 86 | 100 | 100 | 100 |
| LL-D42067α | 0.40 | 15 | 52 | 62 | 89 | 100 | 72 |
| LL-D42067α | 0.20 | 15 | 31 | 24 | 65 | 82 | 0 |
| Infected Untreated Control | 0.0 | 15 | 7.7* | 14* | 9.3* | 1.7* | 11.7* |

*Average lesion score per group of control chicks.

TABLE VI
EVALUATION OF ANTIBIOTIC LL-D42067α AS AN ANTICOCCIDIAL AGENT IN CHICKS

| Compound | Concentration in Diet, ppm | No. Chicks Started | Percent Survival | Percent Chicks with Reduced Lesions | |
| --- | --- | --- | --- | --- | --- |
| | | | | E. tenella | E. acervulina |
| LL-D42046α | 5.0 | 5 | 60 | 100 | 100 |
| LL-D42067α | 2.5 | 5 | 100 | 100 | 100 |
| LL-D42067α | 1.25 | 5 | 100 | 80 | 80 |
| LL-D42067α | 0.75 | 5 | 100 | 40 | 60 |
| LL-D42067α | 0.4 | 5 | 100 | 0 | 0 |
| LL-D42067α | 0.2 | 5 | 80 | 0 | 0 |
| Infected Untreated Control | 0.0 | 20 | 25 | 0 | 0 |
| LL-D42067α | 1.0 | 4 | 100 | 100 | 100 |
| LL-D42067α | 0.75 | 5 | 100 | 100 | 100 |
| LL-D42067α | 0.50 | 5 | 100 | 100 | 100 |
| LL-D42067α | 0.25 | 5 | 80 | 20 | 60 |
| Infected Untreated Control | 0.0 | 20 | 40 | 0 | 0 |

EXAMPLE 5
Evaluation of test compounds as anticoccidial agents in chicks

The usefulness of antibiotic LL-D42067α is demonstrated by its anticoccidial activity against a variety of coccidia species causing disease in chicks according to the following test.

Eighty times the recommended concentration of a commercial anticoccidial vaccine containing mixed species of Eimeria was presented by direct inoculation into the crops of all chicks. Chicks were ten days of age at time of inoculation. Two days before inoculation, medicated feed with several levels of drug was presented to the various groups of chicks. Six days after inoculation, the test was terminated, and the intestinal tracks of the chicks were examined for lesions. A score was assigned to each chick depending upon the presence or absence of lesions and their severity, ranging from 0 to 4 per bird, times the number of birds per

What is claimed is:
1. A method for the control of protozoan infections in warm-blooded animals, said method comprising: administering to the animals a protozoacidally-effective amount of a compound of the formula,

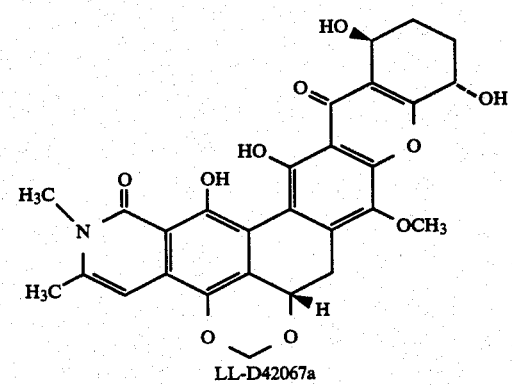

LL-D42067a or a pharmaceutically and pharmacologically acceptable salt thereof.

2. A method according to claim 1, wherein the warm-blooded animals are meat-producing animals, the protozoan infection is coccidiosis, and the anticoccidial agent has the formula,

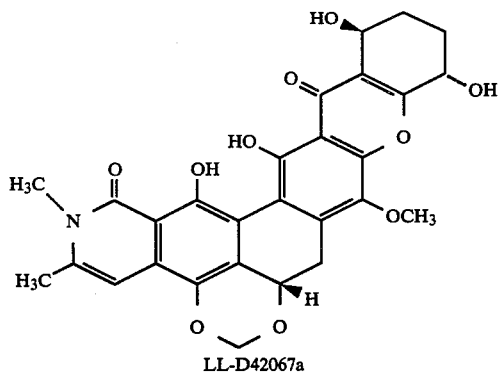

LL-D42067a or a pharmaceutically and pharmacologically acceptable salt thereof; and the anticoccidial agent is orally administered to the meat-producing animals in a solid or liquid carrier containing 0.1 ppm to 100 ppm of the anticoccidial agent.

3. A method according to claim 1, wherein the warm-blooded animals are meat-producing animals, the protozoan infection is coccidiosis, and the anticoccidial agent has the formula,

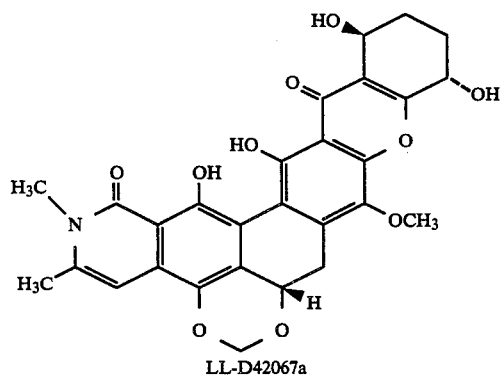

LL-D42067a or a pharmaceutically and pharmacologically acceptable salt thereof; and the anticoccidial agent is parenterally administered to the animals in a solid or liquid carrier containing 0.1 ppm to 100 ppm of the anticoccidial agent.

4. A method according to claim 1, wherein the protozoacidally-effective compound is administered to the animal in a dose range of from 0.003 mg/kg of body weight/day to about 3.0 mg/kg of body weight/day.

5. A method according to claim 2, wherein the animals are poultry; and the anticoccidial agent is administered thereto in feed or drinking water containing 0.1 ppm to 5.0 ppm of the anticoccidial agent.

6. A method according to claim 2, wherein the animals are cattle, sheep, or swine; and the anticoccidial agent is administered thereto in feed or drinking water containing 1.0 ppm to 100 ppm of the anticoccidial agent.

7. An animal feed or animal feed premix composition for the control of coccidiosis infections in meat-producing animals, said animal feed or animal feed premix comprising: a solid edible carrier; and about 0.00001% by weight to about 5.0% by weight of a compound of the formula,

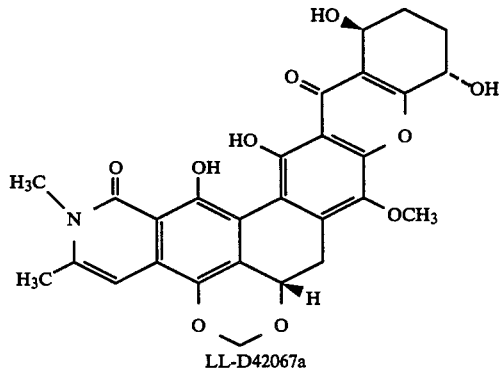

LL-D42067a or a pharmaceutically and pharmacologically acceptable salt thereof.

8. An animal feed or animal feed premix composition according to claim 7, wherein said animals are poultry; and said composition comprises: about 0.00001% by weight to about 0.0005% by weight of a compound of the formula,

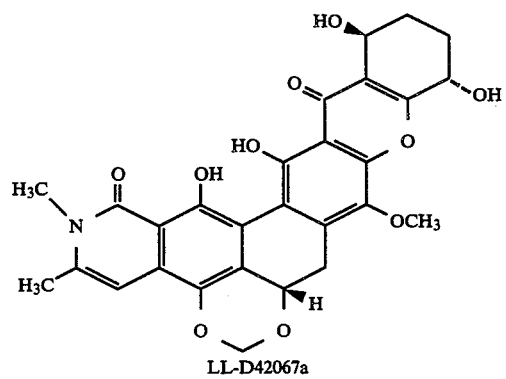

LL-D42067a or a pharmaceutically and pharmacologically acceptable salt thereof.

* * * * *